United States Patent [19]

Golba et al.

[11] 4,448,943

[45] May 15, 1984

[54] METHOD FOR MEASURING POLYMERIZATION PROCESS VARIABLES

[75] Inventors: Joseph C. Golba, Saratoga; Marion G. Hansen, Schenectady, both of N.Y.

[73] Assignee: General Electric Company, Schenectady, N.Y.

[21] Appl. No.: 374,585

[22] Filed: May 3, 1982

[51] Int. Cl.³ .................. C08G 63/62; C08G 73/10
[52] U.S. Cl. ........................... 526/59; 436/85; 523/303; 524/114; 524/140; 524/141; 524/143; 524/600; 524/611; 524/701; 524/710; 524/752; 526/60; 526/61; 526/88; 528/125; 528/126; 528/128; 528/172; 528/179; 528/180; 528/181; 528/182; 528/185
[58] Field of Search ..................... 526/59-61, 526/88; 523/303; 524/114, 140, 141, 143, 405, 611, 600, 701, 710, 752; 528/125, 126, 128, 172, 185, 175-182; 436/85

[56] References Cited

U.S. PATENT DOCUMENTS

| 2,844,568 | 7/1958 | Mertz ................................. 526/59 |
| 3,130,187 | 4/1964 | Tolin et al. ......................... 526/59 |
| 3,254,965 | 6/1966 | Ogle .................................... 526/59 |
| 3,321,280 | 5/1967 | Trotter et al. ..................... 526/59 |
| 3,846,073 | 11/1974 | Baum et al. ......................... 436/85 |
| 4,153,766 | 5/1979 | Koide et al. ........................ 526/59 |

FOREIGN PATENT DOCUMENTS

| 2432654 | 1/1976 | Fed. Rep. of Germany ........ 526/59 |
| 54-104322 | 2/1979 | Japan .................................... 526/59 |
| 274357 | 9/1970 | U.S.S.R. ................................ 526/59 |

*Primary Examiner*—Lester L. Lee
*Attorney, Agent, or Firm*—Richard J. Traverso; James C. Davis, Jr.; James Magee, Jr.

[57] ABSTRACT

A method for determining the concentration of ingredients and other process variables in a polymerization process by measuring the capacitance and dissipation factor of the mixture and determining its dielectric constant at various stages of the process. By the use of an automatic capacitance bridge and a computer, the process variables can be determined and controlled in a matter of seconds.

15 Claims, 7 Drawing Figures

METHOD FOR MEASURING POLYMERIZATION PROCESS VARIABLES

BACKGROUND OF THE INVENTION

Cross-reference to hereby made to Ser. No. 374,588 which is filed concurrently herewith and assigned to the same assignee as the present invention.

The present invention relates to a method or process for determining the concentration of ingredients and other variables in a polymerization process, and, more particularly, the present invention relates to a process for determining the concentration of ingredients and other vairables in a polymerization process by determining the dielectric constant of the polymerization mixture.

Polycarbonates and the process for producing polycarbonates are well known. Generally, such a process comprises reacting a bisaryl carbonate, dihydricphenol, using various types of catalysts in the presence of an organic solvent. Such a process is a batch process. A recitation of such a traditional process, for instance, is to be found in the disclosure of Schnell, U.S. Pat. No. 3,022,272. Recently, a more innovative process has been developed for the production of polycarbonates without the utilization of a solvent. Generally, this process comprises reacting bisphenol-dianhydride with diphenyl carbonate without the presence of a solvent and in the presence of certain metal hydride catalysts containing aluminum hydride or boron hydride ions. Generally, such process comprises mixing the bis(aryl) carbonates and dihydric phenol in the proper proportions and measuring the concentration of the ingredients in the mixture to see that there is the proper concentration of ingredients. Then the catalyst is added to the mixture and the concentration of the catalyst is measured to see that it is within proper concentration. Then, preferably, the different types of stabilizers utilized in such compositions are added, and the concentration of stabilizers that are present in the mixture is measured. The entire mixture is passed through a series of reaction chambers so as to gradually polymerize and form the polycarbonate while at the same time stripping off the by-product phenol. When the polymerization process is completed, the mixture is filtered and is preferably cast into the desired form before it is cooled to form the solid thermoplastic polycarbonate mass. This process is a continuous polymerization process and has many advantages in terms of reducing the cost of labor necessary to produce the finished polycarbonate mass. Some examples of disclosures which relate to such a polymerization process for the production of polycarbonate thermoplastic material without the utilization of a solvent and utilizing the novel metal hydride catalysts are disclosed in the application of Daniel J. Brunelle, Ser. No. 106,856 which was filed Dec. 26, 1979, and which was abandoned as of July 9, 1981, and of which a continuation-in-part is Ser. No. 258,124, which was filed on Apr. 27, 1981, now U.S. Pat. No. 330,664. Other disclosures in this area are that of Brunelle, Ser. No. 106,855, which was filed on Dec. 26, 1979, now abandoned and Brunelle, Ser. No. 134,705, which was filed on Mar. 27, 1980, now U.S. Pat. No. 4,310,656. The patent applications above are given as background. For more details as to the continuous process, reference is to the above patent applications.

The previous process for producing such polycarbonates is a batch process in that all the ingredients are weighed or measured and inserted into a reaction kettle and then the mixture is allowed to react in the proper polymerization degree. The desired polymerization degree was determined by taking out samples every now and then and measuring the intrinsic viscosity of the reaction mixture. By determining the intrinsic viscosity of the reaction mixture, it was possible to determine the molecular weight of the reaction mass and thus the degree of polymerization that had taken place. When there was a sufficient degree of polymerization, the reaction was terminated and the mass of polymerized polycarbonate was filtered to remove impurities and cast in the desired form in which it was to be sold. However, when the instant process was devised as disclosed in the foregoing patent applications, it was desirable that a more rapid means of determining concentration of ingredients as well as the degree of polymerization be used. Thus, in such a continuous process, it was necessary to know if the proper amounts of monomer was mixed together, if the proper amounts of catalysts and stabilizers were mixed into the monomer mixture and if the proper degree of polymerization had taken place at each step along the continuous polymerization process. The only means available to carry out the analysis of the ingredients and degree of polymerization that was known was the use of the intrinsic viscosity measurements for degree of polymerization and for the use of gas chromotography and infrared analysis for the concentration of ingredients and various catalysts and stabilizers. However, such analytical methods, especially the gas chromotgraphy and infrared, were highly undesirable for the continuous polymerization process since this required taking a sample from the process run, taking it to the lab, having it analyzed, and then making the necessary adjustments to the process. Such analytical procedure would keep the process from being truly continuous. Accordingly, it was highly desirable to find a means for measuring such a polymerization process of polymers in a continuous and almost instantaneous manner so that the variable could be determined within seconds at the most, and so that the necessary changes could be made to the process variables. This would allow the proper amount of ingredients to be mixed and the proper polymerization to be carried out in the reaction chambers to produce the desired polymer.

In another vein, the fact that various polymers have various dielectric constants, which can be determined as recognized values, is well known. It is also well known that this dielectric constant of certain thermoplastic and thermosetting polymers would change as the degree of polymerization changed. A discussion of such phenomena is found to be in the publication of Hedwig, entitled *Dielectric Spectroscopy of Polymers,* John Wiley & Sons, 1977. Note especially Chapters 6 and 7. However, the discussion of Hedwig's is just a broad general commentary without appearing to have any specific information with respect to measuring the variables in a process for producing polymers by determining the dielectric constant of the mixture at various stages in the process. There does not specifically appear to be any discussion of the polymerization of polycarbonates and polyetherimides. Further, there is a disclosure of the determination of the $\beta$ staging of thermosetting polymers of the measurement of dielectric constants as disclosed in the publication Sanjana, entitled "The Use of Dielectric Analysis in Characterizing the Degree of B-staging and Cure of Composites," International Conference on Polymer Processing, August, 1977, MIT press (1978).

However, this reference does not go into thermoplastic polymers and as stated previously, there is no discussion of polycarbonates of polyetherimides and how the dielectric measurement could be utilized to determine the process variables, that is the concentration of ingredients and degree of polymerization in a continuous polymerization process.

Accordingly, it is one object of the present invention to provide a method for determining the concentration of ingredients in a continuous polymerization process.

It is another object of the present invention to provide a method for determining almost instantaneously the concentration of ingredients in a continuous polymerization process and utilizing such determinations to control the concentration of the mixture.

It is an additional object of the present invention to utilize capacitance measurements to determine and control the concentration of ingredients in a continuous process for producing polyetherimides.

It is yet an additional object of the present invention to provide a method fo almost instantaneously determining the concentration of ingredients and ionic impurities in a continuous polymerization process for producing thermoplastic materials.

It is still a further object of the present invention to almost instantaneously determine the ionic impurities in a mixture of ingredients and the concentration of the ingredients in a mixture of ingredients as well as the degree of polymerization in a continuous polymerization process of thermoplastics by measuring the dielectric constant and dissipation factor.

This and other objects of the present invention are accomplished by means of the disclosure set forth hereinbelow.

SUMMARY OF THE INVENTION

In accordance with the objects there is provided by the present invention a method for controlling continuous polymerization process variables comprising: (1) mixing at least one monomer and optionally additives to form a mixture; (2) polymerizing the mixture to form a polymer; (3) determining the dielectric constant of the polymer; and (4) controlling the process variables so as to obtain a dielectric constant which is substantially the same as the dielectric constant of the desired polymer.

Utilizing this method, there can be determined almost instantaneously the amount of catalysts, and the flow of catalysts into the mixing chamber that is utilized for mixing the catalyst into the monomer mixture can be controlled. Also, by this method, there can be measured and controlled the concentration of stabilizers or other ingredients. Additionally, this method may also be utilized to measure and control the rate of polymerization. Finally, by using measurements made at several different frequencies, there can be measured the amount of ionic impurities in the mixture, and if the amount of impurities is too large in the batch, the material that is going into the mixing chamber can be diverted so that it can be further purified, and better material can be caused to flow into the first mixing chamber, that is, one having ionic impurities whithin the required parameters.

Finally, the instant process for measuring and controlling concentration of ingredients can be applied to any continuous polymerization process of thermoplastic polymers having sufficient polarity to generate a dielectric constant. It should be noted that although the process is specifically disclosed for polycarbonates and polyetherimides, it can be applied to other situations where two or three monomers are reacted in a continuous manner to produce with or without catalysts, a thermoplastic polymer. The present method of determining and/or controlling the concentration of ingredients and ionic impurities can be applied to the continuous polymerization process of any monomers for the production of a thermoplastic polymer which has sufficient polarity in its ingredients and its reaction polymer mixture during the polymerization process to have measured capacitance value on an automatic capacitance bridge.

DESCRIPTION OF THE PREFERRED EMBODIMENT

As noted above, the present process can be utilized to measure the concentration of all different kinds of organic monomers both in their initial mixed stage as well as degrees of polymerization of the monomers and finally the final end product. This process can be applied to even substantially non-polar materials. Further the present method can certainly be applied to measuring the concentration of polar substances and mixtures of polar and non-polar substances. The foregoing concentrations are measured by measuring the dielectric constant of the material during a given point in the process of mixing the ingredients, or during the polymerization of the polymer. In order to understand how this is done, it is necessary to consider some of the mathematical equations with respect to electric circuits and mathematical equations with respect to the measure of capacitance. Capacitance, in terms of the dielectric constant can be defined as follows:

$$C = \epsilon_a' \frac{A}{H} = \epsilon' \frac{(\epsilon_o' A)}{H}$$

Where
C = capacitance in picofarads
A = capacitance cell plate area in centimeters$^2$
H = gap between plate in centimeters
$\epsilon'$ = dielectric constant
$\epsilon_a'$ = absolute permittivity in picofarads per centimeter
$\epsilon_o'$ = permittivity of vacuum in picofarads per centimeter It is noted that by determining the capacitance and knowing the plate area and the gap between the plates, the dielectric constant can be determined. This dielectric constant will vary for different mixtures of monomers and for different steps in the polymer process, as well as for mixtures in which there are present catalysts and other stabilizer ingredients in the process. It will also differ during various parts of the polymerization process. Preferably, the dielectric constant which is a function of frequency is measured at a constant frequency range of 20 kiloHertz or above to as high as 1 megaHertz. Most preferably, the frequency of measurement is from 20 kiloHertz to 200 kiloHertz. It should be noted that below 20 kiloHertz of frequency, the ions in the mixture may add to the dielectric constants and such ions will respond in sufficiently fast rate to register in the dielectric constant material. Above 20 kiloHertz the ions and other secondary electronic phenomena will not respond sufficiently fast to the frequency and accordingly will be blocked out from the dielectric constant measurement or the capacitance measurements. This threshold value of 20 kiloHertz is given only for monomers and monomer mixtures used for synthesis of polycarbonates and will vary among monomers and polymer systems depending on the viscosity of the ingredients.

Figure 2:
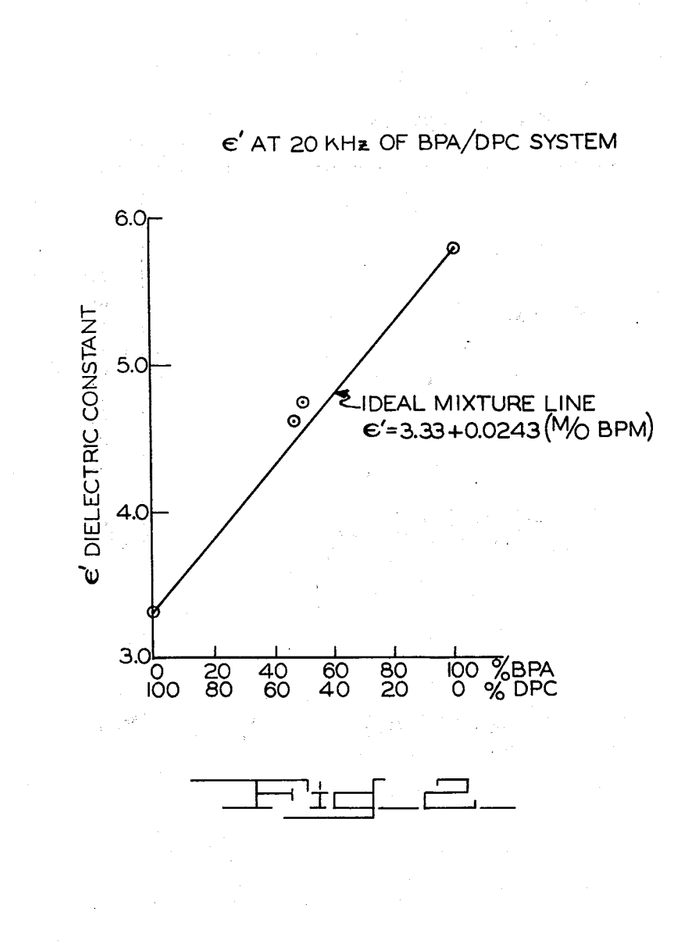
FIG. 2 and FIG. 3 are plots of dielectric constant versus concentration of monomers.
Figure 3:
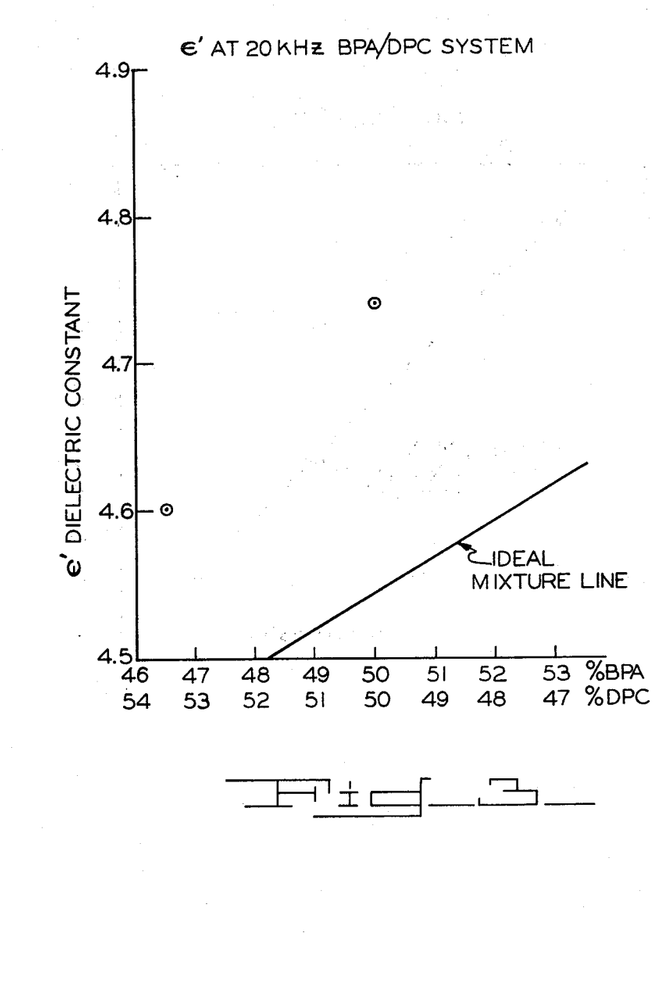

By utilizing this method in the case of the preparation or polymerization of diphenylcarbonate with a dihydric phenol, there can be determined the weight ratio of monomers and the degree of polymerization, as well as the concentration of catalysts within an accuracy of ±0.001 mole fraction. The simplest way this is done is to take known concentrations of ingredients of monomers and different concentrations of catalysts and stabilizers and measure the concentration of monomers by gas chromotography and liquid chromotography and concentrations of cataylst stabilizers, and ionic impurities by conbustion analysis followed by atomic absorption, colorimetric analysis, and ion chromatography. Degree of polymerization is determined by intrinsic viscosity, gel permeation chromatography and vapor pressure osmometry. Then the dielectric constant of the material is determined. By utilizing such analytical techniques, there can be made a plot of, for instance, monomer ratio versus dielectric constant, that is a calibration curve as shown in FIG. 2 and FIG. 3. This can be done for different polymerized mixtures and for different mixtures containing various amounts of catalysts, and for mixtures containing various amounts of stabilizers if such materials are part of the process. The reference in the application above will be made to the specific ingredients used to make the polycarbonate products known by the trademark "Lexan®", which is a trademark of the General Electric Company, and which polycarbonates are produced by reacting diphenyl carbonate with dihydric phenols such as bis-phenol-A.

Having curves such as in FIG. 2 and FIG. 3, one then can, by measuring the dielectric constant of the mixture, determine the concentration of monomers. By having plots such as in FIGS. 2 and 3, it is possible to go manually from receiving the dielectric constant to the calibration curve and note the concentration of the monomers and then proceed to adjust the valves that control the flow of monomers into the first mixing chamber and to the monomer mixing chamber. One can then adjust it to have the proper concentration of monomers which is desired to come out of the first mixing chamber.

In the same way, calibration curves can be made for the presence of catalysts in the mixture further down the process line, as will be explained below, and also the presence or insertion of one or more stabilizers into the monomer mixture. Similar calibration curves can be made for the various polymerization steps or polymerization levels in the process. That is, the material in the continuous process will go from one reaction chamber to another reaction chamber and it is desirable to known the degree of polymerization in each reaction chamber so that if the reaction mixture is not at the proper polymerization level, the variables can be changed. That is, the agitation, the vacuum, the temperature and the amount of phenol removed can be increased or decreased to obtain the necessary degree of polymerization in each reaction chamber, and, finally, the final degree of polymerization at the end of the continuous process. It should be noted and it must be appreciated that the present measuring process is most advantageous for a continuous polymerization process since it will give the dielectric constant, and, if necessary, this can be manually translated to a concentration and the adjustment made to the necessary valves manually. However, this entire conversion to a calibration curve and the adjustment of the process variables can also be made by a computer. By the use of an automatic capacitance bridge, the dielectric constant of the mixture can be determined almost instantaneously and then translated to a concentration level which can then allow the computer to give the necessary instructions to the different components of the processing equipment, so that process variables are adjusted accordingly. By this means it is possible to fine-tune a process so that the desired polymerized polymer is obtained at the terminal end of the process.

The instant process can also be utilized to determine the ionic impurities in the monomer mixture. This can be done by operating and measuring its capacitance at a frequency of less than 20 kiloHertz and preferably between 0.1 to 10 kiloHertz. Again, this frequency value will vary from monomers and polymers to different monomers and polymers. In order to understand how the ionic impurities can be measured, it is necessary to look at a few mathematic equations again with respect to current in an alternating voltage capacitor parallel circuit equipment configuration.

If applying alternating voltage, V(t)
where $V(t) = V_o \exp i\omega t$
where $V_o$ = maximum voltage magnitude
where $\omega$ = angular frequency
where $t$ = time
to get current, I(t) across the capacitor
where $$I(t) = d\frac{[C_x V(t)]}{dt}$$

where $I(t) = I_c(t) + I_L(t)$, a complex current,
and I(t) = current across capacitor plates.

It should be noted that the $I_c(t)$ current is the capacitance component of the current, or the imaginary part of the complex current I(t). $I_L(t)$ is the loss (or resistive) component of the current, or the real part of the complex current I(t). When $I_L(t)$ is greater than zero, a power loss or energy dissipation will occur. Tan$\delta$, the dissipation factor, is equal to $I_L(t)/I_c(t)$.

Alternatively, $I(t) = [i\omega\epsilon' + \omega\epsilon''] C_o V(t)$
thus $I_c = \omega C_o \epsilon' V(t)$
and $I_L = \omega C_o \epsilon'' V(t)$ Accordingly, tan$\delta$, the dissipation factory by definition is equal to $$\frac{I_L}{I_c} = \frac{\omega C_o \epsilon'' V(t)}{\omega C_o \epsilon' V(t)} = \frac{\epsilon''}{\epsilon'}$$

It should be noted that the $\epsilon''$ is equal to the loss factor while $\epsilon'$ is the dielectric constant. Accordingly, the electrical equivalent of a material in a capacitance cell may be analyzed in a simple parallel circuit.
where $\epsilon' = C_x/C_o$
where $C_o$ = the capacitance in vacuum in picofarads and $C_x$ = the capacitance of the material.
Circuit analysis yields $$\epsilon'' = 1/R_x \omega C_o$$

$$\tan\delta = 1/R_x C_x \omega$$

where
  $R_x$ = resistance of the circuit in ohms
  $C_x$ = capacitance of the material
  $\omega$ = angular frequency It is desirable that such a capacitance cell parallel circuit be applied in the instant case in the measurement of capacitance for dielectric constant of the material, and measurement of dissipation factor of the material to determine the concentration of the ingredients and determine the concentration of ionic impurities in polymerization processes, as well as any other variable measurements. The resistance $R_x$ then breaks down as follows:

$$1/R_x = 1/R_i + 1/R_d$$

where $R_i$ is the resistance due to ionic conduction and $R_d$ is the resistance due to nonionic conduction. Thus, substituting in the previous equations $$\tan\delta = 1/R_i C_x + 1/\omega R_d C_x$$

By definition, $R_i$ is constant, not a funtion of frequency, while $R_d$ is a function of frequency. If there is a region where the plot of $\log_{10} \tan\delta$ vs. $\log_{10} \omega$ yields a plot with a slope of $-1$, then there is only ionic conductivity contribution; $R_d$ will be absent. In a region of ionic conductivity $$R_i = 1/\omega C_x \tan\delta$$

It is noted that an automatic capacitance bridge measures $\tan\delta$ and $C_x$ and the $\omega$ frequency is known. Accordingly, the $R_i$ can easily be determined in the area of ionic conductivity by an automatic capacitance bridge measuring the capacitance and dissipation factor for a particular monomer or polymer mixture. It should be noted further that $$R_i = \rho H/A$$

where H and A are as previously defined and where
  $\rho$ = resistivity (ohm cm)
In addition, the ionic concentration is defined by
  Ions concentration = $1/\rho \epsilon \mu$
where
  $\epsilon$ = electronic charge in coulombs (or volt second-/ohm)
  $\mu$ = ion mobility in cm$^2$/volt/second For a particular ion species, the electric charge and the ion mobility will be constant. Accordingly, all that will vary is $\rho$ and accordingly by knowing $\rho$ the ion concentration can be calculated. Further, since $R_i$ is a function of $\rho$ a different method would be to produce a calibration curve, that is to take monomers with different ions in them of different concentrations and calculate and measure the capacitance and the $\tan\delta$. Another way of saying it is to measure the $R_i$ for different known ion concentrations and ionic impurities at different concentrations to determine the $R_i$ and then plot the $R_i$ versus the ionic concentration of different ions. With this plot, then, during an actual process with the use of an automatic capacitance bridge, there can be measured the $R_i$ and thus by manually noting the $R_i$ in the calibration curve, the ionic concentration and the type of ionic impurities can be determined. If the ionic concentration is not within the limits desired, then that paricular batch of material can be diverted from going into the mixing kettle and be sent back to be further purified by distillation while new material is inserted into the first mixing chamber. As with the previous control of monomers this can be done by computer, that is, the automatic capacitance bridge can determine the $C_x$ and $\tan\delta$ of the mixture at several frequencies, the computer can determine the $R_i$ and proceed to determine from the calibration curve the concentration of ionic impurities and with that value make the adjustments necessary to the inputs to the first mixing chamber into which the monomers are put.

Figure 4:
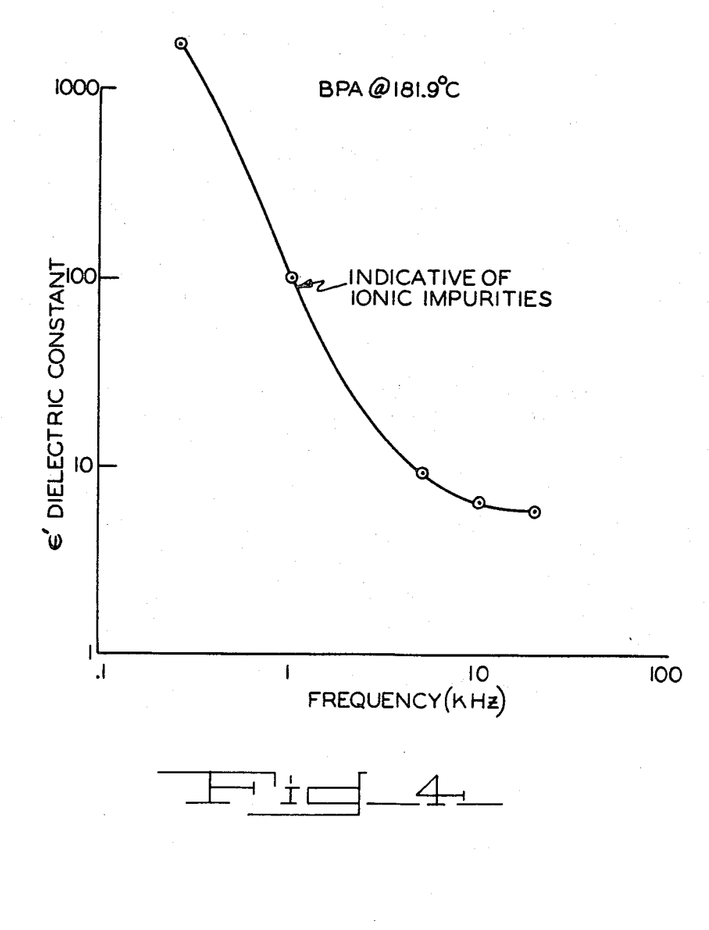
FIG. 4 is a plot of dielectric constant versus frequency for bisphenol-A.
Figure 5:
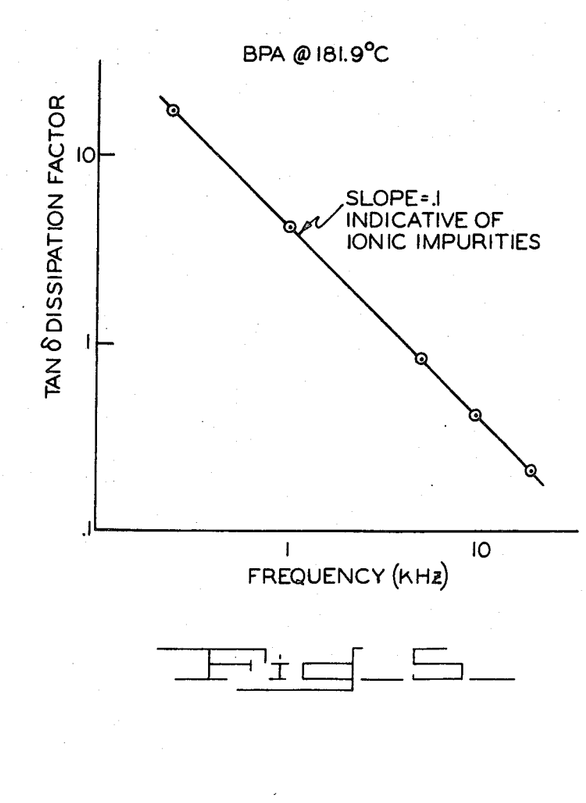
FIG. 5 is a plot of tan δ versus frequency for bisphenol-A.

An automatic capacitance bridge is necessary in this case since the readings must be taken rapidly and must be determined rapidly and further an automatic bridge determines the $\tan\delta$ that is the dissipation factor. FIGS. 4 and 5 are plots of dielectric constant versus frequency for bisphenol-A at 181.9° C. As the curve indicates, the dielectric constant varies with frequency up to 20 kiloHertz thus indicating that the dielectric constant is so-called pure material, is affected by the ionic impurities in the material, and will vary at different frequencies. Also, for this frequency range, there is a plot of the $\tan\delta$ for the same material at the same temperature, with a slope of $-1$. Therefore, the concentration of the ionic impurities can be determined in accordance with the previous equations.

There are similar curves with respect to diphenyl carbonate at similar temperatures which indicate again that the concentration of ions in diphenyl carbonate can be determined by measuring $R_i$.

Figure 6:
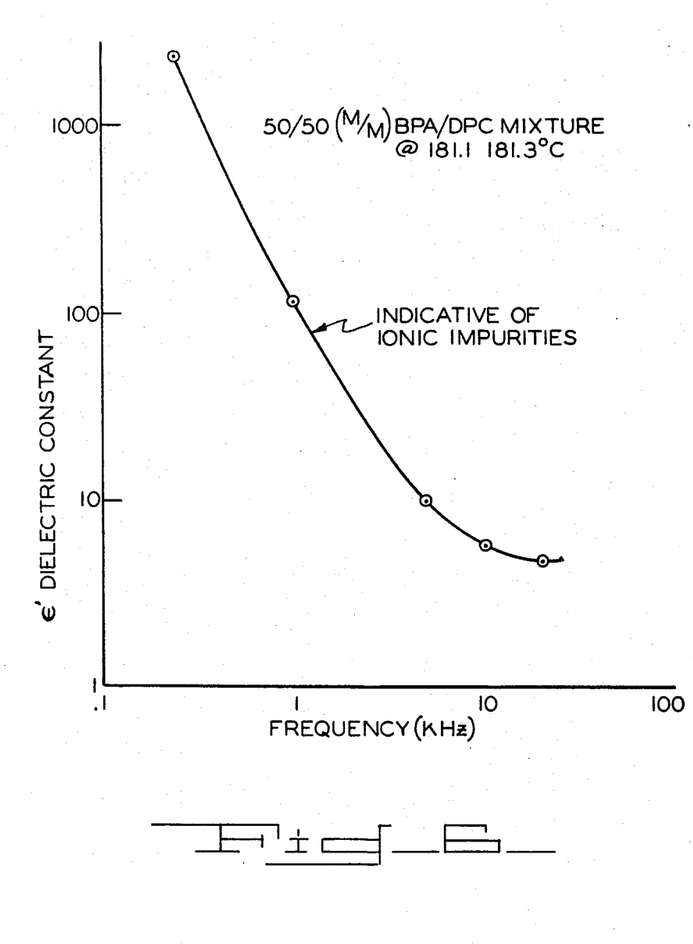
FIG. 6 is a plot of dielectric constant versus frequency for mixture of monomers.
Figure 7:
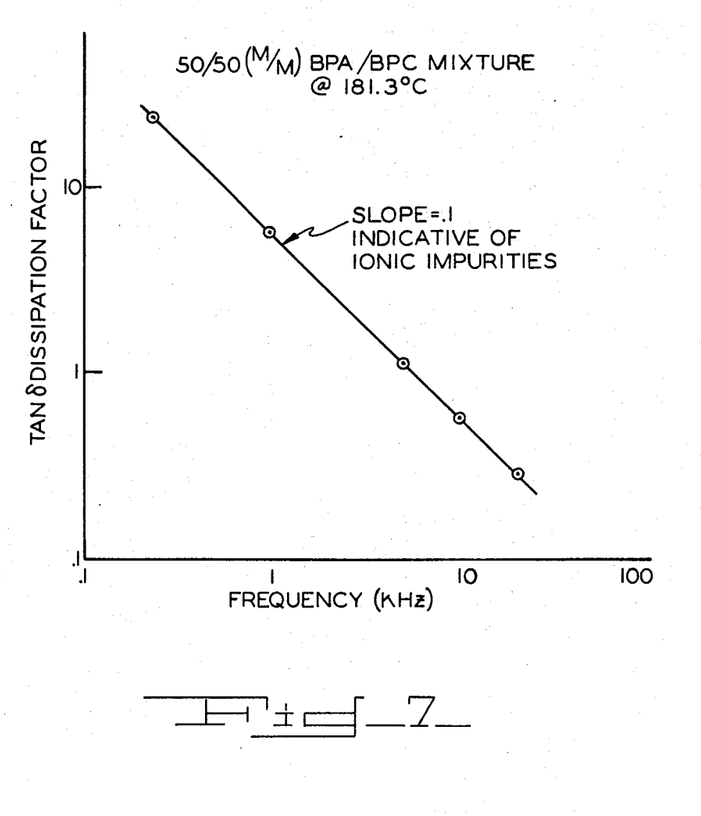
FIG. 7 is a plot of tan δ versus frequency for a mixture of monomers.

As FIGS. 6 and 7 indicate, there were also obtained similar plots for a 50—50 mixture of bis-phenol-A and diphenyl carbonate at a temperature of 181.1° to 181.3° C., that is a 50—50 mole mixture at frequencies from 0.254 to 20 kiloHertz. There was also obtained a slope of $-1$ for the $\tan\delta$ in that frequency range for such a molar mixture of bis-phenol-A and diphenyl carbonate indicating that the dielectric constant in that frequency range would vary due to an ionic impurity in the monomers and that such impurities could be measured by determining the $\tan\delta$ and the capacitance of the mixture. For different mixtures at different ionic impurities, there can be obtained a calibration curve which could result in the determination, by measuring $\tan\delta$ and capacitance through an automatic capacitance bridge, of the ionic concentration and the type of ionic impurities almost instantaneously, and that by utilizing such information, either manually or through a computer adjustments could be made so that the material could continue to be introduced into the first monomer mixing chamber, or the material could be diverted to be further purified, with new material being sent into the first mixing chamber. Further, all of the foregoing determinations of $\tan\delta$ and dielectric constant vary with the frequency for a particular monomer. A plot of the frequency versus dielectric constant for polycarbonate monomers indicates that as one approaches 20 kiloHertz, the activity of the ions or contribution of the ions to the dielectric constant of the material is blocked out such that as the frequency goes above 20 kiloHertz, only the dielectric constant of the material is measured. However, below the frequency of 20 kiloHertz, the current of the ionic impurities is contributed to the dielectric constant.

Although a calibration curve was not produced for the ionic impurities in the instant invention in accordance with the mathematical analysis set forth above, and in accordance with the curves obtained from FIGS. 4 and 5 and FIGS. 6 and 7, there is no reason why the above mathematical analysis should not work and the above procedure should not operate to determine ionic impurities and concentration of ionic impurities in a monomer mixture of the foregoing bisphenol-A and diphenyl carbonate, and in any other materials that behave in a similar manner. In the process it was envisioned that this measurement would desirably be applied to initially determine impurities in the monomers in a continuous polymerization process for producing polycarbonates. It should also be noted that $\tan\delta$ will vary for different monomers and with the concentration of ingredients. In addition, for bisphenol-A and diphenyl carbonate, $\tan\delta$ reaches a peak and then decreases.

In the process for producing polycarbonates there are preferred bis(aryl) carbonates, also commonly referred to as carbonic acid aromatic diesters, which are well known and include illustratively those described by Fox's Formula III in U.S. Pat. No. 3,158,008, column 2, lines 23–72 and column 3, lines 1–42. Presently preferred are bis(aryl)carbonates including diphenyl carbonate, dicresyl carbonate, bis(2-chlorophenyl) carbonate, the bis-phenol carbonates of hydroquinone, resorcinol, and 4,4′-dihydroxy-diphenyl, the bis-phenol carbonates of the bis(4-hydroxyaryl)alkanes, cycloalkanes, ethers, sulfides, sulfones, etc.

Illustratively, "dihydric phenols" include dihydric or dihydroxy aromatic compounds—also incorporated herein by reference—defined by Fox's Formula II in U.S. Pat. No. 3,153,008, column 2, lines 23–72 and column 3, lines 1–42. Presently preferred dihyric phenols are of the formulas:

where independently each R is hydrogen, $C_{1-4}$ alkyl, methoxy, bromine and chlorine, $R_g$ and $R_h$ are hydrogen or a $C_{1-30}$ monovalent hydrocarbon or hydrocarbonoxy group, and where independently each R is as defined above and each Z is hydrogen, chlorine or bromine, subject to the proviso that at least one Z is chlorine or bromine.

Specific examples follow:
4,4′-dihydroxy-diphenyl-1,1-butane,
4,4′-dihydroxy-diphenyl-2-chlorophenyl methane,
4,4′-dihydroxy-diphenyl-2,2-propane also known as "BPA" or bis(4-hydroxyphenyl) propane-2,2,
4,4′-dihydroxy-3-methoxy-diphenyl-2,2-propane,
4,4′-dihydroxy-3-isopropyl-diphenyl-2,2-propane,
4,4′-dihydroxy-diphenyl-2,2-nonane,
4,4′-dihydroxy-2,2′,3,3′,5,5′,6,6′-octamethyldiphenyl methane,
4,4′-dihydroxy-2,2′-dimethyl-5,5′-di-tert.-butyl-diphenyl methane,
4,4′-dihydroxy-3,3′,5,5′-tetrachloro-diphenyl-2,2-propane,
4,4′-dihydroxy-3,3′,5,5′-tetrabromo-diphenyl-2,2-propane,
1,1-dichloro-2,2-bis(4-hydroxyphenyl)ethylene,
1,1-dibromo-2,2-bis(4-hydroxyphenyl)ethylene,
1,1-dichloro-2,2-bis(5-methyl-4-hydroxyphenyl) ethylene,
1,1-dibromo-2,2-bis(3,6-n-butyl-4-hydroxyphenyl)-ethylene,
1,1-dichloro-2,2-bis(2-chloro-5-ethyl-4-hydroxyphenyl)-ethylene,
1-bromo-2,2-bis(4-hydroxyphenyl)ethylene,
1,1-dichloro-2,2-bis(2-ethoxy-4-hydroxyphenyl) ethylene, and
1-bromo-2,2-bis(3,5-diphenylether-4-hydroxyphenylethylene.

Illustrative specific examples of inorganic or organic bases that can be employed follow: sodium metal, lithium hydroxide, quaternary phosphonium sodium carbonate, sodium acetate, sodium methylate, sodium tetrasulfide, sodium borohydride, isopropylamine, propanediamine, pyridine, 1,2,2,6,6-pentamethylpiperidine, sodium benzoate, sodium methylate, sodium phenoxide, sodium salts of bisphenol-A, etc.

Presently preferred bases are certain "metal hydride" catalysts—described in greater detail in U.S. Ser. No. 106,856 and U.S. Pat. No. 4,330,664 previously referred to—and include any compound which contains aluminum hydride or boronhydride counter-ions, for example, alkali metal, alkaline earth metal, quaternary ammonium, quanternary phosphonium, or tertiary sulfonium aluminumhydrides or boronhydrides.

An especially preferred metal hydride is the product obtained by forming a homogeneous solution or melt of a metal hydride containing aluminumhydride or boronhydride counterions with a bis(othro-haloaryl)carbonate, an ortho-haloaryl aryl carbonate, or dihydric phenol, subsequently separating any solvent—if used, cooling, and recovering a homogeneous solid preformed mixture of metal hydride and a bis(orthohaloaryl)-carbonate, an ortho-haloaryl aryl carbonate or a phenol, including containuations thereof.

Any amount of base can be employed. In general, effective mole ratios of base, e.g., LiOH, LiAlH$_4$, Me$_4$MBH$_4$, etc. to dihydric phenols are within the range of from about $10^{-8}$ or 1 or even lower to about 1 to 1, or even higher, preferably from $10^{-6}$ to 1 to about 0.02 to 1, and more preferably from $10^{-5}$ to 1 to $10^{-3}$ to 1. Generally, mole ratios of at least $10^{-5}$ to 1 enhance both the reaction rate and the yield of polycarbonate.

Any reaction pressure can be employed, e.g., atmospheric, subatmospheric or superatmospheric. Generally, however, the process is preferably carried out under a reaction pressure of approximately 1 atm. (~760 mm. Hg.) during the initial phase of the reaction with a subsequent pressure reduction to values in the order of 0.1 to 1.0 Hg. (vacuum), or even lower.

Any reaction temperature can be employed. Optimum reaction temperatures are generally within the range of from 80° C. or even lower, to 300° C., or even higher, and more often 120° C. to 260° C.

Any reaction time can be employed. Generally, optimum reaction time periods are from about 0.5 hours or even less to about 24 hours or even more.

There are present ionic impurities in the diphenyl carbonate and the bisphenol-A such as, for instance, NaCl, Na$_2$CO$_3$, NaSO$_4$, KCl, K$_2$CO$_3$, K$_2$SO$_4$, CaCO$_3$, CaSO$_4$, CaCl$_2$, MgCO$_3$, MgSO$_4$, MgCl$_2$, iron oxides, FeCL$_3$, nickel salts and chromium salts, the ionic impurities concentration of which can be measured by the method disclosed above and that if found present in the material in a concentration 1 ppm to 50 mmp, then the material can be diverted and purified further. If the concentration of the impurities is generally below 2 ppm to 5 ppm, then the monomer can be continued to be processed further in the process. There may also be present stabilizers added to the basic mixture prior to the polymerization for various reasons. Examples of such stabilizers are boric acid, alkylaryl phosphites, and epoxides. Note that these stabilizers are added for increasing thermal/oxidative stability. By utilizing such a process, there can be obtained a more desirable polymerized polycarbonate mixture. There may also be added other additives for various reasons, such as, for instance, potassium and sodium salts of aromatic sulfates which function as flame retardants.

The concentration of all these further additives, in addition to the stabilizers and catalysts, may be determined in the mixture prior to polymerization by the method disclosed above; that is by determining the dielectric constant and/or dissipation factor of the mixture and proceeding to a calibration curve where the dielectric constant will give the concentration of the catalyst or the stabilizers, and further additives in the mixture. After each ingredient has been added to the mixture, the mixture should be passed through a separate capacitance cell which will be connected to an automatic capacitance bridge to determine its dielectric constant. The mixture, after it has been prepared, is then processed through various reaction vessels, The process preferably takes place in atmospheric pressure and vacuum so as to facilitate the removal of phenol which is produced as a by-product in the polymerization process.

Accordingly, after each polymerization stage, the mixture may be put through a capacitance cell in which the dielectric constant and/or dissipation factor may be determined, and by proceeding to a calibration curve, the degree of the polymerization of the mixture may be determined. By this means, by computer or manually, the process variables can be adjusted; that is, vacuum, temperature, agitation, degree of removal of phenol, etc., so as to obtain the proper degree of polymerization in the continuous process as the polymer mixture moves from one reaction vessel to another. Although the above process has been disclosed with respect to the production of polycarbonates, it can also be applied to the continuous polymerization or batch polymerization of any other monomers that meet the requirements set forth above, that is that the material have a dielectric constant that can be measured and substantially. All materials have this, even non-polar materials, and with respect to ionic impurities, tanδ, the dissipation factor, has a value of −1 in some area of frequency. The present method is most preferably applied to substances that are somewhat polar, such as for example the Bisphenol-A and the bisphenyl carbonate disclosed above which are utilized to produce polycarbonate thermoplastics. The present process can be utilized with facility even in batch processes since it is a much faster means of determining polymerization degree.

Another mateial that is made batchwise at the present time in a solvent is the polyetherimides which are obtained in a reaction between an aromatic bis(etheranhydride) and organic diamine. The polyetherimides can be made by effecting a reaction between an aromatic bisetheranhydride of the formula, (1)

and organic diamine of the formula,

H$_2$NR$^1$NH$_2$ where R is a member selected from the class consisting of (a) the following divalent organic radicals:

and and (b) divalent organic radicals of the general formula, where X is a member selected from the class consisting of divalent radicals of the formulas, where m is 0 or 1, y is a whole number from 1 to 5, and the divalent bonds of the —O—R—O— radical are equally situated on the phthalic anhydride end groups, e.g., in the 3,3'-positions or the 4,4'-positions, and $R^1$ is a divalent organic radical selected from the class consisting of (a) aromatic hydrocarbon radicals having from 6–20 carbon atoms and halogenated derivatives thereof, (b) alkylene radicals and cycloalkylene radicals having from 2–20 carbon atoms $C_{(2-8)}$ alkylene terminated polydiorganosiloxane, and (c) divalent radicals included by the formula, where Q is a member selected from the class consisting of and x is a whole number from 1 to 5 inclusive.

U.S. Pat. No. 3,847,867 which is incorporated by reference discloses the traditional process for producing such polyetherimides. It should be noted that such polyetherimides lend themselves to be continually polymerized with or without a solvent as is pointed out with respect to the process for producing the polycarbonate thermoplastics. The degree of reaction of polymerization as well as the percentage of monomers and the addition of any stabilizer and additives can be monitored in a continuous process by the method shown above, that is measuring the dielectric constant and/or dissipation factor of the mixture and referring to a calibration curve. Further, although a tanδ plot of such a monomer mixture was not determined, that is the monomers of Formula (1) and Formula (2), there is no reason why this would not have tanδ plot —1 in some frequency range if ionic species where present.

Accordingly, the foregoing methods for determining the ionic impurities in the concentration of monomers and the degree of polymerization in the continuous process should still apply to the continuous polymerization of polyetherimides. In addition, the degree of polymerization of such polyetherimides can also be determined in the batch process by the method of the present invention; that is, measuring the dielectric constant and/or dissipation factor and obtaining the degree of polymerization from a calibration curve. The process variables can thus be adjusted, and this may be done both in a batch process or in a continuous process for the production of polyetherimides either by computer or by manual means after the dielectric constant and tanδ have been obtained by means of an auotmatic capacitance bridge. It should be noted that one type of capacitance bridge that can be used, for instance, is a GenRad Model 1688, Digibridge.

The instant process can be applied either in a batchwise or in a continuous polymerization process to determine the concentration of ingredients, if the capacitance and/or dissipation factor of the mixture is determined at each point after an additional ingredient is added, and it can be utilized to determine the ionic impurities in the mixture. It can also be utilized to determine the degree of polymerization to produce thermoplastic or thermosetting polymers such as the polyetherimides and polycarbonates.

The process has only been reduced to practice through experiment with respect to polycarbonates but it is envisioned it would apply to polyetherimides, and that the methods of the instant case would apply to all organic materials that are utilized to produce polymers and which have some polarity such as the polycarbonates, the bisphenol-A, diphenyl carbonate, the aromatic(bisetheranhydride) and organic diamines as disclosed above. It is envisioned, although not tested, that the process would also apply in the case of substances which have very low polarity or substantially no polarity at all since from theory it is known that even such substances will have dielectric constants and dissipation factors which, although lower valued, can still be measured. Accordingly, the principals of the instant case should apply so that the invention of the instant case can be utilized to measure the mixture of ingredients, ionic impurities and degree of polymerization in the polymerization process of such materials also.

Figure 1:
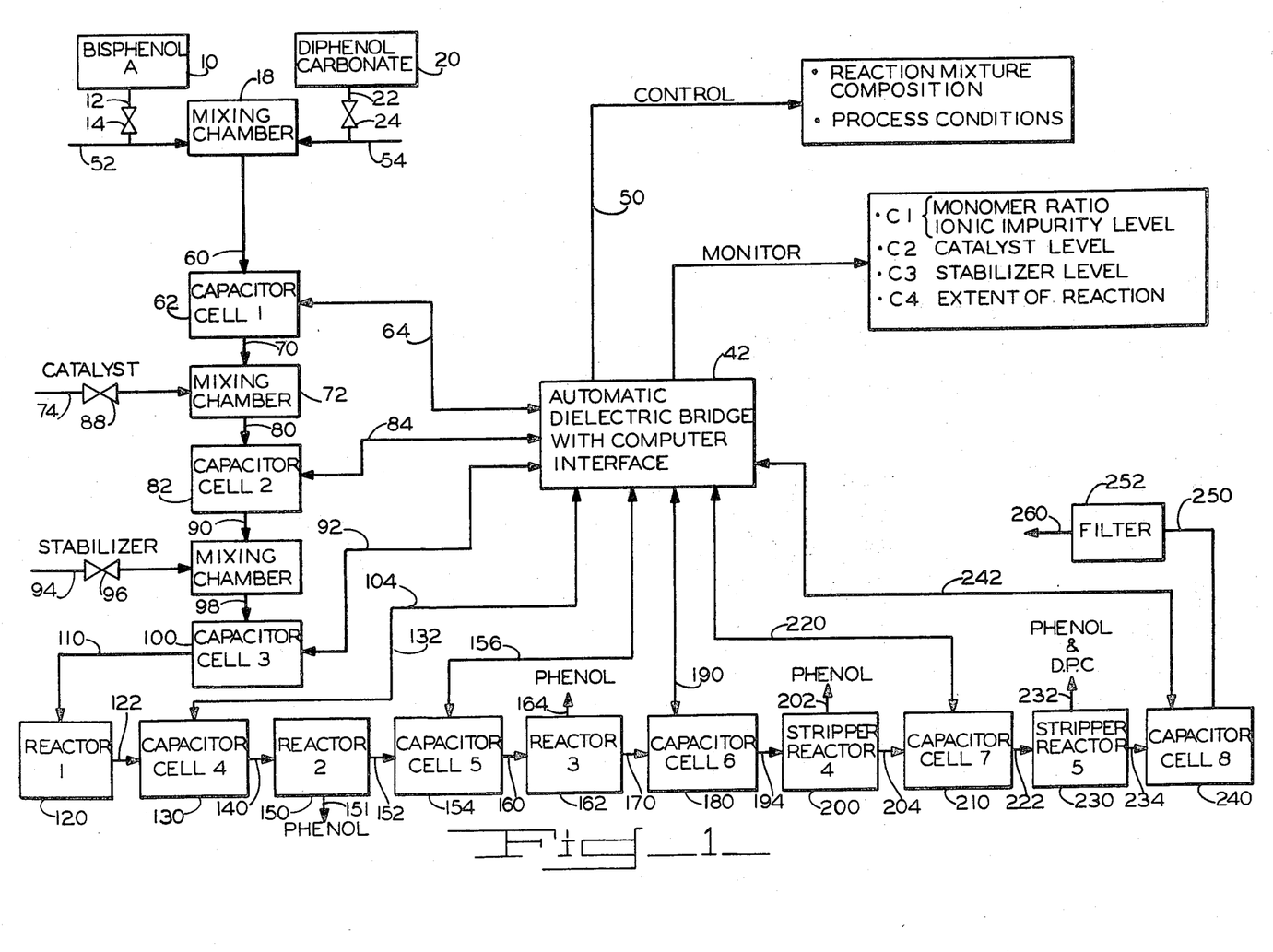
FIG. 1 is a schematic diagram of the preferred process of the instant case.

We will now proceed to FIG. 1 where a preferred description of the process of the instant case will be described, that is, a preferred method of continuously producing polycarbonates as disclosed. The preferred process for the instant case is disclosed for analyzing the addition of ingredients, the ionic impurities, and the degree of polymerization in the production of polycarbonates. This preferred process has not been reduced to practice. It should be noted also that the dielectric constant and the dissipation factor are dependent on temperature as well as frequency. Accordingly, the calibration curves that are obtained will have to be obtained for various temperatures and frequencies, and then the individual or computer will use such calibration curves in a manner well known in the art. This can best be done by a computer which can make a dielectric property profile versus concentration for various temperatures and frequencies from experimental data in a manner well known to a worker skilled in the art.

Further, a measuring device referred to as a dielectric cell may be described as a slit die into which is incorporated a parallel plate capacitance cell. This device is coupled to an automatic digital impedance bridge which measures capacitance and dissipation factor, tan δ. In accordance with the disclosure above, the capacitance is converted either manually or via a computer linked into the dielectric constant and then into a particular concentration of ingredients. It should also be appreciated that even though the description above has been with respect to bispheno-A and diphenylcarbonate, that is a two-monomer polymerization process with a catalyst and stabilizers and other additives, that there may be more than two monomers in the process and the concentration may be measured of the two monomers after they have been mixed and after a third monomer has been mixed, after a fourth monomer has been mixed and so on to yield as desired depending upon how many monomers are used in the process, a concentration determination for the various monomers and other additives utilized in the process. In FIG. 1, which is a schematic diagram of a preferred continuous polymerization process for producing polycarbonates, there is disclosed a preferred present method for analyzing concentration and controlling the concentration of various ingredients, as well as how the polymerization process can be carried out in accordance with the instant invention.

Schematically, bisphenol-A flows from container 10 through line 12 by valve 14 into mixing chamber 18. In addition, at the same time diphenylcarbonate, pumped or forced by whatever means, is continuously fed from container 20 through line 22 by valve 24 into mixing chamber 18. The two monomers are mixed in mixing chamber 18 and then passed through line 60 through capacitor cell 62. There the capacitance of the mixture is measured through electric circuit 64 and automatic dielectric bridge 42, where a computer interface transfers the capacitance of the mixture to a dielectric constant and also measures the dissipation factor tan $\delta$. In accordance with the principles outlined above, the computer determines the ionic impurities in the mixture. If the determination by the computer of the ionic impurities as well as the concentration of such impurities within the mixture is undesirable, then through electric circuit line 50, the computer control turns off one or both of the valves 14 or 24 and opens new valves, not shown, so as to bring new material such as bisphenol-A through line 52 and/or diphenylcarbonate through line 54. The material in container 10 and/or container 20 is taken and processed further so as to bring the impurities within the desired level for utilization in the continuous polymerization process of FIG. 1. These materials in container 10 and/or container 20, depending on the determination of the automatic electric bridge and the computer, are processed further or utilized in the process depending on whether they have the desired level of ionic impurities as determined by the automatic dielectric bridge and computer interface 42. Also, capacitor cell 62, by means of circuit line 64 and automatic dielectric bridge 42, determines the dielectric constant of the mixture, and, by means of the computer interface with the prior calibration curve, makes a determination of the concentration of monomers. If the concentration of monomers is appropriate, or within the ranges permissible set forth in the computer program, then the computer does nothing, but if the mixture of monomers is not within the desired level, then the computer interface through control line 50 changes the settings of valves 14 and 24, for instance in lines 12 and 22 so as to bring the flow of bisphenol-A and diphenyl carbonate into mixing chamber 1 within the proper stoichiometric levels which are desired for polymerization reactions. The material then proceeds from capacitor cell 62 through line 70 into mixing chamber 72. A metal hydride is brought in, such as boron hydride, disclosed in the foregoing Brunelle patent applications as a catalyst in through line 74 into mixing chamber 72. A uniform mixture is continuously obtained, and exits out of mixing chamber 72 through line 80 into capacitor cell 82. In capacitor cell 82, and through line 84, the capacitance and dissipation factor are measured and determined by an automatic dielectric bridge with computer interface 42, and along with the prior calibration curves there is determined the concentration of the catalyst and the mixture of ingredients passing through capacitor cell 82. If the mixture of catalysts passing into capacitor 82 is within the prescribed levels, then the computer interface control does nothing. If it is not within the desired prescribed limits, then the dielectric bridge with computer interface 42 sends through electric line 50 control signals to valve 88 in line 74 so as to increase or decrease the amount of catalysts going through line 74 into mixing chamber 72.

Proceeding from capacitance cell 82, the catalyzed mixture passes through line 90 into mixing chamber 92. A stabilizer such as boric acid is fed into mixing chamber 92 through line 94 by valve 96 where the stabilizer is uniformly mixed with the other ingredients. The resulting uniform mixture continuously passes through line 98 into capacitor cell 100 where the capacitance and dissipation factor are measured by means of cell 100, line 104 and the automatic dielectric bridge with computer interface 42. The computer interface converts the capacitance to a dielectric constant and compares it and the measured dissipation factor with a prior determined calibration curve, whereupon from such comparison there is determined the concentration of the stabilizer in the mixture. If this is in accordance with the prescribed limits set in the instructions to the computer, then the computer does nothing, but if the concentration of the stabilizer is above or below the required limits, then through computer interface 42, control line 50 activates valve 96 to either increase or decrease the flow of the stabilizer through line 94 into mixing chamber 92. From capacitor cell 100, the mixture then continuously passes through line 110 into the first reactor, 120. The mixture, after passing through reactor 120, then passes through line 122 and through capacitor cell 130. The capacitor cell 130, line 132 and automatic dielectric bridge with computer interface 42 determine the dielectric constant and dissipation factor of the partially polymerized mixture, and when this is compared to a calibration curve for the particular temperature of the mixture passing through the dielectric cell, as well as the frequency of the applied field across the cell, then the degree of polymerization is determined by the computer. The computer then does nothing if the degree of polymerization is within the prescribed limits. However, if it is not within the prescribed limits, then the computer, through control line 50 and other control lines not shown, adjusts the variable conditions in the first reactor, 120, so as to vary the process conditions such as temperature, pressure, rate of removal of phenol, agitation, etc., so as to arrive at the proper polymerization degree in reactor 120. From capacitor cell 130, the mixture then passes through line 140 into the second reactor, reactor 150. From reactor 150, the mixture passes through line 152 through capacitor cell 154. Capacitor cell 154 measures the capacitance and dissipation factor of the mixture passing through it, and through electric line 156 passes the signal to the automatic dielectric bridge with computer interface 42 which determines the dielectric constant. Using this parameter and/or the measured dissipation factor and comparing it to a calibration curve determines the degree of polymerization. If this is within the required levels, then the dielectric bridge with computer interface 42 does nothing. If it is not within the prescribed limits, then computer interface 42 sends a signal through line 50 and other lines, not shown, so as to control the variables in reactor 150 to obtain the desired degree of polymerization. In reactor 120, no phenol is stripped off. Phenol is continually stripped off as a by-product through line 151 in reactor 150. From capacitor cell 154 the partially polymerized mixture passes through line 160 into reactor 162, where again the mixture is agitated and polymerized continuously. Phenol is removed continuously from reactor 162 through line 164. From reactor 162, the mixture passes through line 170 into capacitor cell 180. Capacitor 180 connected through line 190 into dielectric bridge 42, measures the capacitance and dissipation factor, and, along with the computer interface, converts capacitance to dielectric constant and compares it and the dissipation factor to prior calibration curves. If the polymerization degree is within the prescribed levels, computer interface 42 does nothing. If it is not, then through line 50 and other control lines, not shown, the process variables in reactor 162 are changed so as to obtain the proper polymerization degree desired from the mixture coming out of reactor 162 through line 170. From capacitor cell 180, the mixture passes through line 194 into stripper reactor 200.

From stripper reactor 200 which is agitated, phenol is removed, and unreacted diphenylcarbonate is removed through line 202. The mixture then passes from stripper reactor 200 through line 204 into capacitor cell 210. From capacitor cell 210, connected to automatic dielectric bridge 42 through electric line 220, the capacitance and dissipation factor are determined. The computer interface converts capacitance to dielectric constant and compares it and the measured dissipation factor to prior calibration curves to determine the degree of polymerization as well as the excess unreacted monomers by subtraction. Then, from cell 210, the mixture passes through line 222 into stripper reactor 230 which is the last reactor in the continuous polymerization cycle.

Phenol is continually being stripped off, and diphenylcarbonate is continually removed through line 232; the phenol and diphenylcarbonate are stripped off at this point should be the last of these monomers. Preferably, in the continuous polymerization process of diphenyl carbonate and biphenol-A, the polymerization should be substantially completed. The amount of phenol and diphenylcarbonate remaining in the polymer mixture emanating from reactor 230 through line 234 should be the amount desired in the final product, and the polymerization should be substantially completed. From line 234 the mixture passes into capacitor cell 240 where the capacitance and dissipation factor of the mixture passing through capacitance cell 240 are measured using the automatic dielectric bridge 42 connected by means of electric line 242. If the material is completely polymerized in accordance with the prescribed calibration curve, and the phenol and diphenylcarbonate are removed to the degree desired and the automatic dielectric bridge computer interface 42 will do nothing. However, if the polymerization is not completed in reactor 230 and the desired amount of phenol and diphenylcarbonate are not removed, then through line 50 and other lines, computer interface 42 will send signals so as to change the process variables in reactor 230. From capacitor cell 240, the polymerized mixture passes through line 250 through filter 252 to remove undesired salts.

Then the polymerized mixture may be passed from filter 252 through a dielectric cell, not shown, where the capacitance can be measured further to see that the necessary amount of the salts has been removed by the filter and if not to make adjustments to the filter or utilize a new filter if the one in the line is not operating properly. The material then passes from filter 252 through line 260 to casting and storage prior to shipment. The foregoing processes for analyzing concentrations of various ingredients in polymerization reactions, as well as for controlling those conditions, have been shown for the proposed polycarbonate continuous polymerization process.

In accordance with the above principles and reductions to practice, the foregoing method of measuring concentration of ionic impurities and ingredients of a polymerization process can be applied to other variations of this process and even to the present batch process for producing polycarbonates. The foregoing FIG. 1 is a schematic diagram for a proposed method for continuously polymerizing polycarbonates. Insofar as applicable to the present case, it describes how this process could be monitored and controlled continuously, utilizing the invention of the instant case. It should also be noted that all of the information on the polycarbonate process has not been recited above, since such is not the invention of the instant case. Only so much as is necessary for the instant disclosure has been disclosed.

The examples below are given for the purpose of illustrating the reduction to practice of certain aspects of the present invention. They are not given below for setting limits and boundaries to the instant invention.

The dissipation factor (tan $\delta$) may also be used in some cases to determine the concentrations of ingredients and degree of polymerization. In the case of polycarbonates the tan $\delta$ increases with concentrations of ingredients in a determinable manner, reaches a peak and then decreases. Accordingly, if the concentration values fall on one side of the curve, that side of the curve could be used to determine the concentration of ingredients. These factors apply in the determination of degree of polymerization for polycarbonates. However, the polymerization process of other polymers may not peak in tan$\delta$, and tan$\delta$ may be used much more easily to determine concentration of ingredients and degree of polymerization.

EXAMPLE 1

The dielectric response of bisphenol-A, diphenyl carbonate, a 50/50 (mole/mole) mixture of bisphenol-A and diphenyl carbonate (stoichiometric composition with respect to polymerization reaction), and a 46.49/53.51 (mole/mole) mixture of bisphenol-A and diphenyl carbonate (15 mole percent excess diphenyl carbonate with respect to polymerization reaction) was determined. Each material was melted and heated to a nominal temperature of 181° C. poured into a Balsbaugh LD-3 three terminal, guarded electrode capacitance cell, also maintained at a nominal temperature of 181° C. in a Ransco Model SD30-1 temperature test chamber. The capacitance cell was electrically connected to Gen-Rad Model 1688 Precision LC Digibridge which was electrically connected to a Hewlett-Packard Model 5150A Thermal Printer. Temperature was independently measured using a type K thermocouple, electronically compensated, and electrically connected to a Fluke Model 8024A multimeter. The capacitance and dissipation factor were determined at several frequencies and the capacitance was converted into dielectric constant. The data generated is listed in Tables I through IV. FIGS. 4 through 7 show log-log plots of dielectric constant and dissipation factor (tan$\delta$) versus frequency for bisphenol-A and 50/50 (mole/mole) mixture of bisphenol-A and diphenyl carbonate. Diphenyl carbonate and the 46.49/53.51 (mole/mole) mixture of bisphenol-A and diphenyl carbonate behave in a similar fashion. In every case tested the dielectric constant was observed to decrease as frequency was increased, and asymptotically approached some constant value at frequencies greater than 20 kiloHertz, i.e., approached the intrinsic dielectric constant of the material under test. The response of the dielectric constant at frequencies less than 20 kiloHertz is indicative of the presence of ionic impurities. The presence of ionic impurities was conclusively demonstrated by the log-log plots of tan$\delta$ versus frequency. The $-1$ slope observed in these plots is an accepted test for ionic species contribution to the dielectric response of a material. Since no ionic species were intentionally added to the materials tested, their detected presence was attributed to residual ionic species not removed during the purification step during the preparation of the bisphenol-A and diphenyl carbonate.

A plot of the intrinsic dielectric constant, i.e., the dielectric constant as measured at frequencies of 20 kiloHertz, versus concentration of bisphenol-A or diphenyl carbonate is shown in FIG. 2. An expanded portion of FIG. 2 is shown in FIG. 3. The functionality between dielectric constant and composition is nonideal as indicated by the nonlinear form which increases from a low value with pure diphenyl carbonate to a high value with pure bisphenol-A. However, this functionality is monotonic and constitutes a unique relationship between dielectric constant and monomer mixture composition, i.e., bisphenol-A and diphenyl carbonate. The accuracy and precision of these measurements indicate a monomer mixture composition resolution of 0.1 percent or 0.001 mole fraction.

The dissipation factor (tan$\delta$) measurements made at several frequencies are not only useful for detecting the presence of ionic species but when used in accordance with capacitance measurements using the procedures outlined above can be used to determine the concentration of said ionic species even when their concentration level is of parts per million order of magnitude.

TABLE I

DIELECTRIC MEASUREMENTS ON DIPHENYL CARBONATE AT 181.35 $\pm$ 0.05° C.

| Frequency (kHz) | Capacitance (pF) | Dielectric Constant | Tan $\delta$ |
|---|---|---|---|
| 0.240 | 6090 | 561 | 13.12 |
| 1.000 | 385.6 | 35.5 | 3.16 |
| 5.000 | 49.1 | 4.5 | 0.63 |
| 10.000 | 38.5 | 3.5 | 0.32 |
| 20.000 | 36.1 | 3.3 | 0.16 |

TABLE II

DIELECTRIC MEASUREMENTS ON A 53.51/49.49 (MOLE/MOLE) MIXTURE OF DIPHENYL CARBONATE AND BISPHENOL-A AT 181.9 $\pm$ 0.2° C.

| Frequency (kHz) | Capacitance (pF) | Dielectric Constant | Tan $\delta$ |
|---|---|---|---|
| 0.240 | 30880 | 2846 | 26.10 |
| 1.000 | 1811 | 167 | 6.26 |
| 5.000 | 117.0 | 10.8 | 1.26 |
| 10.000 | 63.6 | 5.9 | 0.64 |
| 20.000 | 49.9 | 4.6 | 0.33 |

TABLE III

DIELECTRIC MEASUREMENTS ON A 50/50 (MOLE/MOLE) MIXTURE OF DIPHENYL CARBONATE AND BISPHENOL-A AT 181.2 $\pm$ 0.1° C.

| Frequency (kHz) | Capacitance (pF) | Dielectric Constant | Tan $\delta$ |
|---|---|---|---|
| 0.240 | 25377 | 2339 | 23.05 |
| 1.000 | 1512 | 139 | 5.55 |
| 5.000 | 106.4 | 9.8 | 1.12 |
| 10.000 | 62.3 | 5.7 | 0.56 |
| 20.000 | 51.4 | 4.7 | 0.28 |

TABLE IV

DIELECTRIC MEASUREMENTS ON BISPHENOL-A AT 181.9° C.

| Frequency (kHz) | Capacitance (pF) | Dielectric Constant | Tan $\delta$ |
|---|---|---|---|
| 0.240 | 18189 | 1676 | 17.41 |
| 1.000 | 1098 | 101 | 4.17 |
| 5.000 | 100.8 | 9.3 | 0.83 |
| 10.000 | 69.9 | 6.4 | 0.41 |
| 20.000 | 62.5 | 5.8 | 0.21 |

What is claimed is:

1. A method for controlling continuous polymerization process variables comprising (1) mixing at least one monomer and optionally additives to form a mixture; (2) polymerizing the mixture to form a polymer; (3) monitoring the dielectric constant of the mixture; and (4) controlling the process variables so as to obtain a dielectric constant which is substantially the same as the dielectric constant of the desired polymer.

2. The method of claim 1, wherein the monomers are selected from the class consisting of Bisphenol-A, diphenyl carbonate, aromatic bis(etheranhydride)s and meta-phenylene diamine.

3. The method of claim 1, wherein the additive is a metal hydride catalyst selected from the class consisting of aluminum hydride, boron hydride and mixtures thereof.

4. A method of claim 1, wherein the additive is a stabilizer selected from the class consisting of boric acid, phosphates and epoxides.

5. The method of claim 1 wherein the process variables include reactant and additive concentration, reaction temperature and reactor residence time.

6. The method of claim 1 wherein the dielectric constant is determined by means of an automatic capacitance bridge.

7. The method of claim 6, wherein the capacitance is measured at a frequency of 20 kiloHertz to 1 megaHertz.

8. The method of claim 1 or 6, wherein the process variables are controlled by means of a computer.

9. The method of claim 1 or 3, further comprising mixing into said mixture any number of other monomers and additives one at a time, wherein after each new mixture is formed, the dielectric constant of the new mixture is determined and the amount of additive or monomer adjusted so as to obtain the dielectric constant of a mixture containing the desired concentration of monomer or additives.

10. The method of claim 1, wherein the degree of polymerization of the polymer is controlled.

11. A method of claim 1 wherein the dissipation factor of the polymer is determined from capacitance measurements and is used to determine process variables.

12. The method of claim 11, wherein the concentration of ionic impurities is determined from the dielectric constant and dissipation factor, and used to control which batch of monomer and the rate at which said batch of monomer is introduced into said mixture.

13. In a method for controlling process variables in a continuous polymerization process in the manufacture of polycarbonates from bisphenol-A and diphenyl carbonate monomer, the improvement comprising monitoring the dielectric constant and dissipation factor of the reaction mixture, determining the concentrations of the reactants and additives and degree of polymerization of said polymer, and controlling the amount of monomers and additives and processed variables based on said determinations.

14. In a method for measuring and controlling continuous polymerization process ingredients in the manufacture of polyetherimides from an aromatic bis(ether-anhydride) monomer and an aromatic diamine monomer, the improvement comprising monitoring the dielectric constant and dissipation factor of the reaction mixture, determining the concentrations of the reactants and additives and the degree of polymerization of said polymer, and controlling the amount of monomers and additives and process variables based on said determinations.

15. The method of claims 13 or 14 wherein the capacitance is measured at a frequency of 20 kiloHertz to 1 megaHertz.

* * * * *